United States Patent [19]

Mitani et al.

[11] Patent Number: 4,503,246

[45] Date of Patent: Mar. 5, 1985

[54] PROCESS FOR PREPARATION OF GLYOXYLIC ACID

[75] Inventors: Tadayuki Mitani; Mamoru Endo, both of Arai, Japan

[73] Assignee: Daicel Chemical Industries, Ltd., Sakai, Japan

[21] Appl. No.: 326,296

[22] Filed: Dec. 1, 1981

[30] Foreign Application Priority Data

Dec. 1, 1980 [JP] Japan .................................. 55-169256
Aug. 12, 1981 [JP] Japan .................................. 56-126146

[51] Int. Cl.$^3$ ...................... C07C 51/16; C07C 59/153
[52] U.S. Cl. ...................................... 562/531; 562/577
[58] Field of Search ................................ 562/531, 577

[56] References Cited

U.S. PATENT DOCUMENTS

| | | | |
|---|---|---|---|
| 2,443,118 | 6/1948 | Plump | 562/531 |
| 3,281,460 | 10/1966 | Gandon | 562/531 |
| 3,661,986 | 5/1972 | Washecheck | 562/531 |

*Primary Examiner*—Vivian Garner
*Attorney, Agent, or Firm*—Flynn, Thiel, Boutell & Tanis

[57] ABSTRACT

A process for the preparation of glyoxylic acid is disclosed which comprises reacting an aqueous solution of glyoxal with chlorine. The reaction is preferably carried out under pressure, under the condition that the hydrochloric acid concentration in the aqueous solution of glyoxal is 1 to 15%. The reaction can be carried out in the presence of a catalytically effective amount of bromine as a catalyst.

14 Claims, No Drawings

PROCESS FOR PREPARATION OF GLYOXYLIC ACID

The present invention relates to a process for preparing glyoxylic acid by oxidation of glyoxal.

A well-known process for the preparation of glyoxylic acid comprises the electrolytic reduction of oxalic acid. This process, however, is disadvantageous from an industrial viewpoint because the reaction cannot be carried out at a high concentration because oxalic acid has a low water solubility, the equipment expenses for such a process are high, and the selectivity or current efficiency is reduced if the current density or conversion of oxalic acid is increased.

As a process for preparing glyoxylic acid by oxidation of glyoxal, a nitric acid oxidation process is most frequently used. In this process, the selectivity is high, but the conversion of the starting glyoxal is low. If the conversion of glyoxal is increased, oxalic acid is formed and the selectivity of the reaction to produce glyoxylic acid is drastically reduced. For example, if the conversion of glyoxal is increased from 70% to 90%, the selectivity of the reaction to produce glyoxylic acid is reduced from 90% to 70%.

In the nitric acid oxidation process, a considerable period of time is required for completing the reaction of the nitric acid, and the reaction progresses under conditions wherein nitric acid accumulates in the reaction mixture. Accordingly, good control of the reaction cannot be attained by adjusting the rate of charging the nitric acid into the reaction mixture. Furthermore, if the nitric acid oxidation is halted part way through the reaction, the results obtained on resumption of the reaction are extremely poor and the selectivity is particularly lowered. Accordingly, there cannot be employed an embodiment of the nitric acid oxidation process in which a first-stage reaction is carried out at a lower conversion, which involves no risk of reduction of the selectivity, and wherein a minute adjustment is then conducted by incorporation of additional nitric acid to obtain the desired conversion. Moreover, when the reaction is temporarily halted for some reason or other, the reaction cannot conveniently be resumed. This disadvantage is observed not only when the reaction is interrupted, but also generally in nitric acid oxidations of aqueous solutions of glyoxal containing a large amount of glyoxylic acid.

Another known process for the preparation of glyoxylic acid comprises the electrolytic oxidation of glyoxal (see U.S. Pat. No. 4,235,684). In this process, a selectivity of about 80% can be maintained even if the conversion is increased to about 95%, and this process ameliorates to some extent the defect of the nitric acid oxidation process wherein a high selectivity cannot be obtained at a high conversion. However, in this electrolytic oxidation process, the reaction can scarcely be carried out at high concentrations, and a large stationary installation of equipment is necessary for the reaction.

The present inventors have conducted research with the aim of overcoming the foregoing defects of the conventional processes and providing a process capable of producing glyoxylic acid with high selectivity even at a high conversion, in which the reaction can be easily controlled and does not require a large stationary installation of equipment. It was found that if chlorine is used as the oxidant for oxidizing glyoxal, the foregoing objective can be attained very effectively. The present invention has been completed on the basis of this discovery. Additionally, it was discovered that the results can be further improved by carrying out the above-described reaction in the presence of a catalytically effective amount of bromine.

More specifically, in accordance with the present invention, there is provided a process for the preparation of glyoxylic acid which comprises reacting an aqueous solution of glyoxal with chlorine. This process is represented by the following reaction scheme:

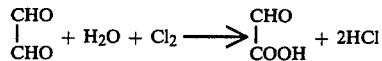

The chlorine that is used as the oxidant in the present invention is elemental chlorine which is produced in large quantities as a by-product in the manufacture of electrolytic soda and is readily commercially available. Diatomic chlorine is a very effective oxidant for achieving the object of the present invention. When glyoxal is oxidized with chlorine, glyoxylic acid can be obtained with a selectivity higher than 80%, even at a high conversion of the starting glyoxal exceeding 90%.

Glyoxal is commonly obtained in the form of an aqueous solution of hydrated glyoxal, and an aqueous solution of glyoxal having a concentration of 5 to 40 wt. % is customarily used in the present invention. Even when an aqueous solution of glyoxal which is inferior in purity to a commercially available glyoxal product is used in the present invention, such as an aqueous solution of glyoxal containing a large amount of glyoxylic acid produced as a by-product in the process for the preparation of glyoxal, the disadvantages encountered in the nitric acid oxidation process do not occur at all, and glyoxylic acid can be obtained in a high yield.

In the process of the present invention, the oxidation reaction can be accomplished by blowing chlorine gas into an aqueous solution of glyoxal, or other gas-liquid contacting apparatuses can be used, such as a bubble column, a packed column or the like. The reaction can be carried out batchwise or continuously. In the process of the present invention, the oxidation reaction can be controlled by adjusting the rate of feeding chlorine into the reaction mixture. The maintenance of the reaction temperature at a constant level and delicate adjustment of the amount of the oxidant for obtaining a desirable conversion can be accomplished more easily than in the nitric acid oxidation process. The reaction is exothermic, and therefore, the desired reaction temperature is customarily maintained by appropriate heat-removing means, such as water cooling. The liquid phase temperature is not particularly critical, but that temperature is ordinarily 0° to 100° C. The reaction progresses sufficiently at a temperature lower than room temperature. However, if the reaction is carried out at a low temperature under atmospheric pressure, the absorption rate of chlorine is relatively low and a long reaction time is required for completion of the reaction. As a means for shortening the reaction time, a high reaction temperature, for example 80° C., can be adopted. In this case, however, the selectivity tends to decrease as the conversion is increased. Accordingly, a medium temperature in the range of 10° to 50° C. is preferred as the reaction temperature.

As a more effective means for shortening the reaction time, the reaction can be carried out under pressure.

When an aqueous solution of glyoxal is reacted with chlorine under superatmospheric pressure, the reaction rate can be increased without detrimental effects on the reaction results. For example, in Example 5 given hereinafter, 58 hours were needed to obtain a glyoxal conversion of 91.4% in a reaction carried out at atmospheric pressure, whereas in Example 6, wherein the pressure was slightly elevated, a conversion of higher than 98% was obtained within 36 hours. In Example 7 the reaction was carried out under a pressure of 2 Kg/cm² gauge, and a conversion higher than 93% was obtained within 14 hours. Furthermore, in each case, the selectivity to glyoxylic acid was high.

If the reaction pressure is increased beyond 2 Kg/cm² gauge, the reaction rate is further increased. The reaction can be carried out under a pressure of 5 to 10 Kg/cm² gauge, if desired. However, in such a case, a high pressure installation becomes necessary and the load for removal of reaction heat is increased. Since the reaction time can be shortened to about 10 hours even under a pressure of 2 Kg/cm² gauge (see Example 9), a pressure higher than this need not be employed.

As shown by the reaction scheme set forth above, hydrogen chloride is produced as a by-product in the process of the present invention, and since the reaction mixture is in the form of an aqueous solution, the hydrogen chloride is present in the reaction mixture in the form of hydrochloric acid and the amount of it present in the reaction mixture increases as the reaction progresses. The reaction rate is influenced by the concentration of hydrochloric acid that is present in the reaction mixture. For example, when the reaction is carried out at 30° C., and the hydrochloric acid concentration exceeds a level of 13 to 15% by weight, the reaction speed is drastically reduced. Accordingly, if the concentration of the starting material is adjusted so that the final hydrochloric acid concentration is lower than 13 to 15% by weight, the conversion of glyoxal can be increased to 90 to 95%, for a reaction time of about 20 hours, under atmospheric pressure or slightly elevated pressure (see Examples 1 and 8). If the reaction pressure is elevated to 2.0 Kg/cm² gauge, the reaction time can be shortened to about 9 to 10 hours (see Example 9). Furthermore, it was unexpectedly found that if the starting glyoxal concentration is lowered in order to control the hydrochloric acid concentration in the reaction mixture, the selectivity of the reaction can also be improved (see Examples 8 and 9).

Extraction, electric dialysis, ion exchange resin treatment or evaporation can also be used to keep the hydrochloric acid concentration in the reaction mixture below 15% by removal of hydrochloric acid. However, the method of limiting the starting glyoxal concentration is very simple and useful in practice.

The hydrochloric acid concentration also has an influence on the yield, based on the chlorine, in the process of the present invention. In the initial stage of the reaction, the yield based on chlorine is abnormally low in the process of the present invention. Accordingly, the mechanism of the oxidation reaction was studied in order to find a way to prevent this undesirable phenomenon. As the result, it was found that when the hydrochloric acid concentration is low, oxidation reactions of oxalic acid or formic acid incorporated in the starting glyoxal occur as side reactions, with the hypochlorous acid that is formed by the reaction represented by the following reaction scheme:

$$Cl_2 + H_2O \rightleftharpoons HOCl + HCl$$

with the result being that the yield based on chlorine is reduced. It was also found that if a certain hydrochloric acid concentration is maintained in the starting aqueous solution of glyoxal, the occurrence of such side reactions can be controlled. At later stages of the glyoxal oxidation reaction hydrochloric acid formed by the reaction that produces glyoxylic acid becomes present in the reaction system, and the above-mentioned problem does not arise. In short, in the process of the present invention, good results can be obtained if a certain minimum hydrochloric acid concentration is maintained in the initial stage of the reaction by the addition of a small amount of hydrochloric acid to the starting aqueous solution of glyoxal. It is preferred that the concentration of the initially added hydrochloric acid is 1 to 2%. If the initially added hydrochloric acid concentration is too high, the reaction rate is reduced as noted previously. In the process of the present invention, it is preferred that the reaction of an aqueous solution of glyoxal with chlorine be carried out at a hydrochloric acid concentration maintained in the range of 1 to 15%. As illustrated in Example 10 given hereinafter, if hydrochloric acid is added to the starting aqueous solution of glyoxal, the yield of glyoxylic acid based on absorbed chlorine is improved and wasteful production of hypochlorous acid by the side reaction is controlled. The result is that the final hydrochloric acid concentration is maintained at 12.8%, which is substantially the same level that is obtained in the case where the reaction is started with 0% hydrochloric acid concentration, and the conversion of glyoxal is about 95% in each case. It is apparent that addition of 1 to 2% of hydrochloric acid to the initial reaction mixture has no adverse effects on the reaction rate.

When glyoxal containing impurities, such as formic acid and oxalic acid, is used as the starting material, and chlorine oxidation is begun with a hydrochloric acid concentration of 0%, the discharge gas in the initial stage contains carbon dioxide gas as an inactive component in an amount of about 80% by volume. Accordingly, the loss of chlorine included in the discharge gas withdrawn in order to maintain the reaction pressure is great. However, if the reaction is carried out at an initial hydrochloric acid concentration of 1%, the content of carbon dioxide gas in the discharge gas in the initial stage of the reaction is less than 30% by volume, and the loss of chlorine is thereby reduced.

As can be seen from the foregoing description, satisfactory results can be obtained if hydrochloric acid is added so that the initial hydrochloric acid concentration of the reaction mixture is about 1%. Addition of hydrochloric acid in the initial stage of the reaction in an excess amount is not preferred because: (1) when the conversion reaches a high level, the hydrochloric acid concentration is too high and the reaction rate is thereby reduced; (2) the conversion and the selectivity of the reaction become poor; and (3) wasteful production of hydrochloric acid is increased.

Glyoxylic acid is used, for example, in reactions with phenols. When glyoxylic acid formed by the nitric acid oxidation process is used for such a reaction, it is necessary to remove nitric acid from the glyoxylic acid in order to purify the glyoxylic acid because nitric acid contained in the reaction mixture has an adverse effect on the phenol reaction. By contrast, glyoxylic acid obtained according to the present invention can be used for the subsequent phenol reaction directly without difficulty, even though, in the process of the invention, the glyoxylic acid is obtained in the form of an aqueous solution containing hydrochloric acid. If needed, this aqueous solution may be subjected to a hydrochloric acid-removing treatment, such as ion exchange resin treatment, electric dialysis or amine extraction.

The glyoxylic acid concentration in the aqueous solution obtained in the process of the invention depends mainly on the glyoxal concentration in the starting aqueous solution. In the case of the nitric acid oxidation reaction, the obtained aqueous solution is further diluted with water contained in the nitric acid employed as the oxidant. The process of the present invention is advantageous also in this point because the chlorine used as the oxidant does not contain water. In order to obtain an aqueous solution having a glyoxylic acid concentration higher than a level that can be obtained directly by the reaction of the present invention, the aqueous solution of glyoxylic acid can be concentrated by known techniques, if needed.

The present invention will now be described in detail with reference to the following examples. In the examples, all percentage amounts are percent by weight unless otherwise indicated.

EXAMPLE 1

Chlorine gas was blown into 1850.2 g of an aqueous solution containing 5.03% of glyoxal and 0.48% of glyoxylic acid, at 15° to 18° C., for 19 hours, to obtain 1984.3 g of an aqueous solution containing 5.08% of glyoxylic acid, 0.34% of glyoxal and 7.24% of hydrochloric acid.

The conversion of glyoxal was 92.8% and the selectivity to glyoxylic acid was 83.4%.

EXAMPLE 2

Chlorine gas was blown into 829.3 of an aqueous solution containing 14.0% of glyoxal and 1.15% of glyoxylic acid, at 15° to 20° C., for 13 hours, to otain 912.7 g of an aqueous solution containing 9.29% of glyoxylic acid, 5.43% of glyoxal and 10.57% of hydrochloric acid. The conversion of glyoxal was 57.3% and the selectivity to glyoxylic acid was 88.6%.

EXAMPLE 3

Chlorine gas was blown into 1850.0 g of an aqueous solution containing 30.41% of glyoxal and 2.68% of glyoxylic acid, at 15°, for 46 hours, to obtain 2114.3 g of a reaction liquid containing 14.68% of glyoxylic acid, 16.15% of glyoxal and 14.19% of hydrochloric acid. Glyoxylic acid was obtained in an amount of 92.4%, based on the 3.81 mols of glyoxal that was converted by the above reaction.

EXAMPLE 4

Chlorine gas was blown into 2405.1 g of an aqueous solution containing 14.23% of glyoxal and 0.40% of glyoxylic acid, at 80° C., for 24 hours, to obtain 2600.9 g of a reaction liquid containing 8.02% of glyoxylic acid, 6.07% of glyoxal and 9.63% of hydrochloric acid. The conversion of glyoxal was 53.9% and the selectivity to glyoxylic acid was 84.6%.

When blowing of chlorine gas was resumed in this example, no bad effects were caused by the interruption, and a higher conversion was obtained. More specifically, when the reaction was conducted for a total of 32, 40 and 48 hours, the glyoxal concentration was reduced to 4.64, 2.43 and 0.47%, respectively, while the glyoxylic acid concentration was increased to 9.29, 10.04 and 10.51%, respectively, and the hydrochloric acid concentration was increased to 11.6, 12.8 and 16.0%, respectively.

EXAMPLE 5

Chlorine was blown under atmospheric pressure into 2230.6 g of an aqueous solution containing 13.01% of glyoxal and 5.18% of glyoxylic acid, at 30° C., for 58 hours, to obtain 2596.4 g of a reaction liquid containing 0.96% of glyoxal, 14.02% of glyoxylic acid and 14.02% of hydrochloric acid. The conversion of glyoxal was 91.4%, the selectivity to glyoxylic acid was 73.4% and the yield of glyoxylic acid was 74.9%, based on the starting glyoxyl compounds present (the total number of mols of glyoxal and glyoxylic acid in the starting material).

EXAMPLE 6

Chlorine was blown, under a pressure of 0.2 Kg/cm$^2$G, into 2442.8 g of an aqueous solution containing 11.88% of glyoxal and 6.12% of glyoxylic acid, at 30° C., for 36 hours, to obtain 2854.8 g of a reaction liquid containing 0.70% of glyoxal, 14.13% of glyoxylic acid and 16.20% of hydrochloric acid. The conversion of glyoxal was 93.1%, the selectivity to glyoxylic acid was 73.7% and the yield of glyoxylic acid was 77.6%, based on the glyoxyl compounds present in the starting material as noted above.

EXAMPLE 7

Chlorine was blown, under a pressure of 2.0 Kg/cm$^2$G, into 868.0 g of an aqueous solution containing 12.12% of glyoxal and 2.51% of glyoxylic acid, at 30° C., for 14 hours, to obtain 993.4 g of an aqueous solution containing 0.69% of glyoxal, 12.48% of glyoxylic acid and 14.46% of hydrochloric acid. The conversion of glyoxal was 93.5%, the selectivity to glyoxylic acid was 81.4% and the yield of glyoxylic acid was 79.5%, based on the starting glyoxyl compounds present.

EXAMPLE 8

Chlorine gas was blown, under a pressure of 0.2 Kg/cm$^2$G, into 2234.1 g of an aqueous solution containing 9.11% of glyoxal and 3.60% of glyoxylic acid, at 30° C., for 21 hours, to obtain 2522.1 g of an aqueous solution containing 0.56% of glyoxal, 11.29% of glyoxylic acid and 12.68% of hydrochloric acid. The conversion of glyoxal was 93.1%, the selectivity to glyoxylic acid was 84.5% and the yield of glyoxylic acid was 83.7%, based on the starting glyoxyl compounds present.

EXAMPLE 9

Chlorine was blown, under a pressure of 2.0 Kg/cm$^2$G, into 868.9 of an aqueous solution containing 9.32% of glyoxal and 3.46% of glyoxylic acid, at 30° C., for 10 hours, to obtain 975.6 g of a reaction liquid containing 0.65% of glyoxal, 11.45% of glyoxylic acid and 12.47% of hydrochloric acid. The conversion of glyoxal was 92.2%, the selectivity to glyoxylic acid was 85.8% and the yield of glyoxylic acid was 83.8%, based on the starting glyoxyl compounds present.

EXAMPLE 10

Chlorine was blown, under a pressure of 2.0 Kg/cm$^2$G, into 868.0 g of an aqueous solution containing 9.16% of glyoxal, 1.93% of glyoxylic acid and 1.00% of hydrochloric acid, at 30° C., for 8 hours, to obtain 969.4 g of a reaction liquid containing 0.44% of glyoxal, 10.36% of glyoxylic acid and 12.78% of hydrochloric acid. The conversion of glyoxal was 94.7%, the selectivity to glyoxylic acid was 87.1% and the yield of glyoxylic acid was 85.0%. At the end of the intermediate stage 6 hours from the start of the reaction, the conversion was 90.9% and the selectivity was 89.2%. The yield of glyoxylic acid based on absorbed chlorine, which was calculated from the increase in the amount of hydrochloric acid present at the end of the full 8 hour reaction, was 82.1%.

For purposes of comparison, a glyoxal aqueous solution was reacted with chlorine, under a pressure of 2.0 Kg/cm$^2$, at 30° C., in the same manner as described above, except that the initial concentration of hydrochloric acid was 0%. The curve of the rate of increase of the hydrochloric acid concentration with the passing of time was similar to the curve obtained for the reaction above utilizing a starting hydrochloric acid concentration of 1%, except that a delay of about 2 hours was observed. When the reaction was conducted for 10 hours, both the conversion of glyoxal and the concentration of hydrochloric acid were at substantially the same levels as those obtained in the reaction above in 8 hours of reaction time (when the starting material contained 1% of hydrochloric acid). The yield of glyoxylic acid based on absorbed chlorine was 80.0%. The glyoxylic acid yield was adversely influenced by the low hydrochloric acid concentration in the initial stage of the reaction.

When the initial hydrochloric acid concentration was adjusted to 1.5% and 2%, the resultant yield of glyoxylic acid based on absorbed chlorine was 85.4% and 82.4%, respectively.

EXAMPLE 11

Chlorine gas was introduced, at 15° C., for 21 hours, into 500.0 g of an aqueous solution of glyoxal containing 5.25% of glyoxal and 6.76% of glyoxylic acid. As a result, 537.0 g of the reaction liquid was obtained, containing 10.18% of glyoxylic acid, 0.62% of glyoxal and 8.03% of hydrochloric acid. It is found that the amount of glyoxylic acid in the liquid was 16.4 times larger than the weight of glyoxal, corresponding to 81.2 mol % of glyoxal compounds, aldehydes and acids contained in the starting material.

COMPARATIVE EXAMPLE

A solution of 742.4 g of 45% nitric acid was added dropwise into 1500.0 g of an aqueous solution containing 17.84% of glyoxal and 10.50% of glyoxylic acid, at 40° C., over a period of 4 hours. The mixture was aged at 40° C. for 6 hours to obtain 2032.1 g of a reaction liquid containing 17.46% glyoxylic acid and 1.10% glyoxal. The conversion of glyoxal was 91.6% and the selectivity to glyoxylic acid was 63.1%.

The process can be carried out in the presence of bromine as a catalyst. The amount of bromine is from 0.1 to 10 mole %, preferably from 0.5 to 5 mole %, based on the amount of glyoxal used. The bromine can be added in the form of a substance which can produce bromine chloride under the reaction conditions. The substance can be bromine, hydrobromic acid, an alkali metal bromide or bromine chloride. The hydrochloric acid concentration in the glyoxal solution is from 1 to 20 wt. %, in the presence of bromine.

The modification of the invention wherein bromine is involved will be stated in detail by the following examples.

EXAMPLE 12

Chlorine was blown, under a pressure of 2.0 kg/cm$^2$G at 30° C. for 9 hours, into 819.8 g of an aqueous solution containing 9.20% of glyoxal, 0.20% of glyoxylic acid, which had been purified by electrodialysis and mixed with hydrochloric acid so as to have a hydrochloric acid content of 1.5%, in order to obtain 916.6 g of a reaction liquid containing 9.21% of glyoxylic acid, 0.28% of glyoxal and 12.8% of glyoxal and 12.86% of hydrochloric acid. The conversion of glyoxal was 96.6% and the selectivity to glyoxylic acid was 89.0%.

EXAMPLE 13

Chlorine was blown, under a pressure of 2.0 kg/cm$^2$G at 30° C. for 6 hours, in the presence of 12.3 g of sodium bromide, into 748.6 g of the same starting aqueous solution as used in Example 12, to obtain 863.6 g of a reaction liquid containing 9.37% of glyoxylic acid, 0.10% of glyoxal and 13.66% of hydrochloric acid. The conversion of glyoxal was 98.7% and the selectivity of glyoxylic acid was 91.6%.

EXAMPLE 14

Chlorine gas was blown, under a pressure of 2 kg/cm$^2$G at 30° C. for 6 hours, in the presence of 10.4 g of bromine, into 834.6 g of an aqueous solution containing 9.04% of glyoxal, 0.25% of glyoxylic acid and 1.51% of hydrochloric acid, to obtain 948.6 g of a reaction liquid containing 9.27% of glyoxylic acid, 0.10% of glyoxal and 12.9% of hydrochloric acid. The conversion and selectivity obtained were higher values than in Example 12.

EXAMPLE 15

The process was conducted in the same manner as in Example 14, except that an amount of bromine was 1.0 g and the reaction time was 8 hours, to obtain 934.6 g of an aqueous liquid containing 9.24% of glyoxylic acid, 0.23% of glyoxal and 12.62% of hydrochloric acid. The conversion was 97.2% and the selectivity was 90.1%.

EXAMPLE 16

Chlorine gas was blown, under a pressure of 2 kg/cm$^2$G at 30° C. for 9 hours, in the presence of 22.4 g of bromine, into 816.6 g of an aqueous solution containing 19.9% of glyoxal, 0.58% of glyoxylic acid and 1.51% of hydrochloric acid, to obtain 1019.9 g of an aqueous liquid containing 16.68% of glyoxylic acid, 2.84% of glyoxal and 19.1% of hydrochloric acid. The conversion was as high as 82.2%, though the hydrochloric acid concentration was nearly 20%. The selectivity was 97.1%. These results are very high.

The embodiments of the invention in which an exclusive property or privilege is claimed are defined as follows:

1. A process for preparing glyoxylic acid which comprises reacting an aqueous solution of glyoxal with diatomic chlorine gas at a reaction temperature in the range of 0° C. to 100° C.

2. A process according to claim 1, wherein the reaction is carried out under a pressure greater than atmospheric pressure.

3. A process according to claim 1 or claim 2, wherein the starting aqueous solution of glyoxal contains at least about 1 wt. % of hydrochloric acid.

4. A process according to claim 1, wherein the reaction temperature is in the range of 10° to 50° C.

5. A process according to claim 1, wherein the pressure is in the range of from about 2.0 Kg/cm$^2$ gauge to about 10 Kg/cm$^2$ gauge.

6. A process according to claim 1, wherein hydrochloric acid is present in said aqueous solution and the hydrochloric acid concentration of said aqueous solution of glyoxal is maintained in the range of about 1 wt. % to about 15 wt. % throughout the duration of the reaction.

7. A process as claimed in claim 1 or claim 2 in which said aqueous solution of glyoxal contains a catalytically effective amount of bromine as a catalyst.

8. A process as claimed in claim 7 in which the amount of bromine is from 0.1 to 10 mole %, based on the amount of glyoxal used.

9. A process as claimed in claim 8 in which said amount of bromine is from 0.5 to 5 mole %.

10. A process as claimed in claim 7 in which bromine is added in the form of a substance which can produce bromine chloride under the reaction conditions employed.

11. A process as claimed in claim 10 in which said substance is selected from the group consisting of bromine, hydrobromic acid and an alkali metal bromide.

12. A process as claimed in claim 7 in which hydrochloric acid is present in said aqueous solution and the hydrochloric acid concentration of said aqueous solution of glyoxal is maintained in the range of from 1 to 20 wt. % throughout the duration of the reaction.

13. A process for the preparation of glyoxylic acid which comprises reacting an aqueous solution containing about 5–40 wt. % glyoxal and a catalytically effective amount of bromine, with diatomic chlorine gas at a pressure in the range of from atmospheric pressure to 10 Kg/cm$^2$ gauge, wherein an approximately constant temperature in the range of 0° C. to 100° C. is maintained throughout the duration of the reaction, and hydrochloric acid is present in said glyoxal solution in an amount of about 1 to 20 wt. % throughout the duration of the reaction.

14. A process for the preparation of glyoxylic acid which comprises reacting an aqueous solution containing about 5–40 wt. % glyoxal with diatomic chlorine gas, at a pressure in the range of from atmospheric pressure to 10 Kg/cm$^2$ gauge, wherein an approximately constant temperature in the range of 0° to 100° C. is maintained throughout the duration of the reaction, and hydrochloric acid is present in said glyoxal solution in an amount of about 1 to 15 wt. % throughout the duration of the reaction, such that glyoxylic acid is obtained with a selectivity of at least 80% and a conversion ratio of at least 90%.

* * * * *